(12) United States Patent
Teng et al.

(10) Patent No.: US 8,617,490 B2
(45) Date of Patent: Dec. 31, 2013

(54) REACTION CASSETTE, ASSAY DEVICE, AND ASSAY METHOD

(75) Inventors: Kai Tsung Teng, Hsinchu (TW); Yueh-Hui Lin, Hsinchu (TW); Thomas Y. S. Shen, Hsinchu (TW)

(73) Assignee: Apex Biotechnology Corp., Hsinchu (TW)

( * ) Notice: Subject to any disclaimer, the term of this patent is extended or adjusted under 35 U.S.C. 154(b) by 293 days.

(21) Appl. No.: 12/832,030

(22) Filed: Jul. 7, 2010

(65) Prior Publication Data

US 2011/0104731 A1 May 5, 2011

Related U.S. Application Data

(60) Provisional application No. 61/257,537, filed on Nov. 3, 2009.

(51) Int. Cl.
| | | |
|---|---|---|
| *G01N 15/06* | (2006.01) | |
| *G01N 33/00* | (2006.01) | |
| *G01N 33/48* | (2006.01) | |

(52) U.S. Cl.
USPC ............ 422/554; 422/50; 422/68.1; 422/547; 422/550; 422/551; 422/552; 422/559

(58) Field of Classification Search
USPC .......... 422/50, 68.1, 547, 550, 551, 552, 554, 422/559
See application file for complete search history.

(56) References Cited

U.S. PATENT DOCUMENTS

| | | | | |
|---|---|---|---|---|
| 5,162,237 | A * | 11/1992 | Messenger et al. ........... | 436/523 |
| 6,120,733 | A * | 9/2000 | Goodman et al. ............ | 422/430 |
| 7,125,161 | B2 * | 10/2006 | Winkler et al. ............... | 366/144 |
| 8,158,430 | B1 * | 4/2012 | Roy et al. ........................ | 436/16 |
| 2007/0004029 | A1 | 1/2007 | Aoyagi | |

FOREIGN PATENT DOCUMENTS

CN 1892220 1/2007

* cited by examiner

*Primary Examiner* — Brian J Sines
(74) *Attorney, Agent, or Firm* — Liu & Liu

(57) ABSTRACT

A reaction cassette for biochemical assay, a biochemical assay device including the reaction cassette, and a biochemical assay method performed by using the biochemical assay device are provided. The reaction cassette includes a first space, a second space, a third space, and an inner wall. The first space is configured to accommodate liquid and includes a first opening facing upward. The second space includes a second opening whose direction is perpendicular to the direction of the first opening. The first space and the second space are disposed such that when the reaction cassette is rotated, liquid in the first space can flow into the second space. The third space is located under the first space and includes a third opening whose direction is the same as the direction of the first opening. The inner wall connects the second opening and the third opening, which serves as a liquid flow channel between the second space and the third space.

15 Claims, 12 Drawing Sheets

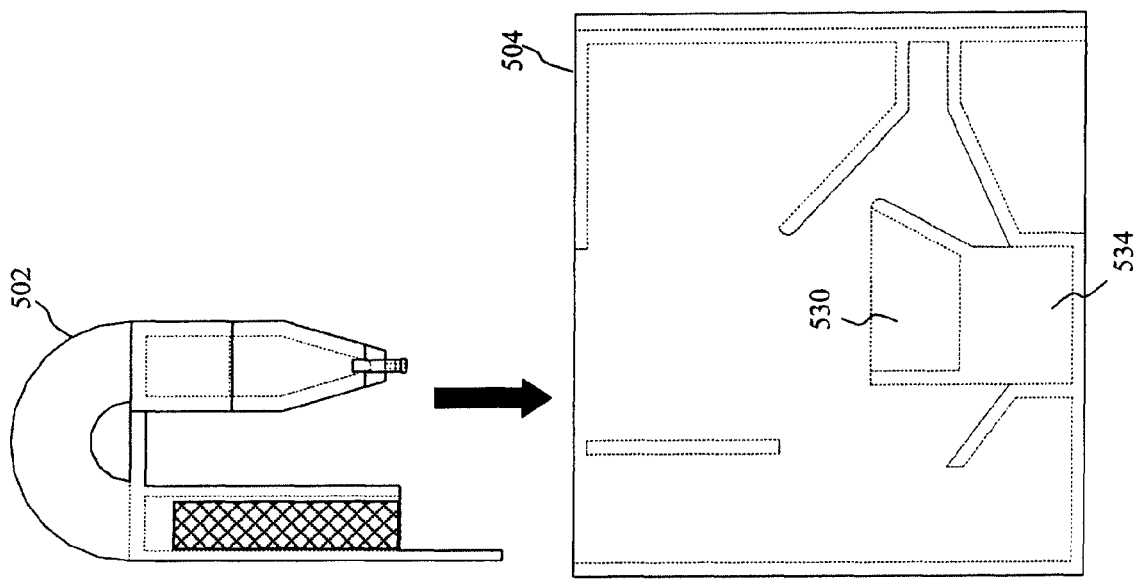

REACTION CASSETTE, ASSAY DEVICE, AND ASSAY METHOD

CROSS REFERENCE TO RELATED APPLICATIONS

This application claims priority to U.S. provisional Application No. 61/257,537 entitled "ASSAY DEVICE AND MEASURING METHOD THEREOF", filed on Nov. 3, 2009, which is incorporated herein by reference in its entirety for all purposes.

FIELD OF INVENTION

The present invention relates to an assay device and an assay method using the assay device, and more particularly, to a biochemical assay device for measuring characteristics of liquid sample and an assay method using the biochemical assay device.

BACKGROUND OF THE INVENTION

In vitro diagnostic (IVD) assay has been widely utilized in the qualitative and quantitative assessment of body fluid for providing information regarding diagnosis and therapy. For this reason, IVD assay has become an increasingly important means in medical industry.

Generally, the forgoing IVD assay techniques require the utilization of assay devices and measurement instruments, as well as the reagent preparation. During the assay procedure, the blood sample or other body fluid samples may need to be collected manually, so that the samples are more likely to be contaminated and risk of infection is highly increased.

Further, different reagents may need to be added sequentially to react with the sample during the assay operation. If these steps are executed by user's direct operation, the procedure may become complicated and take a long time. Besides, there is also a problem in that waste liquid treatment is required after the assay procedure.

Accordingly, it is advantageous to have an assay device and an assay method capable of overcoming limitations of the prior art, such that the measurement process and the waste liquid treatment can be performed easily and securely.

SUMMARY OF THE INVENTION

In view of the problems existing in the prior arts, the present invention provides an assay device for measuring characteristics of liquid sample and an assay method using the assay device. The device and the method of the present invention can be used in various chemical assays, medical assays, or other similar assays having multiple steps of mixing reagents/reactants and sample.

In one embodiment, the device and the method of the present invention can be used to facilitate the examination and analysis process having multiple reaction steps between liquid sample (e.g. blood sample) and reagent (or reactant). According to optical characteristics of the liquid sample after the reaction, the amount of one or more ingredients of the liquid sample can be determined.

According to an aspect of the present invention, a reaction cassette for biochemical assay is provided, which includes a first space, a second space, a third space, and an inner wall. Each of the first space, the second space, and the third space has a function of accommodating liquid. The first space has a first opening whose direction is directed upward, and the second space has a second opening whose direction is perpendicular to the direction of the first opening. The first space and the second space are disposed such that when the reaction cassette is rotated, liquid in the first space can flow into the second space. The third space is located below the first space and has a third opening whose direction is the same as the direction of the first space. The inner wall is connected with the second opening and the third opening for providing a liquid flow channel between the second space and the third space.

According to another aspect of the present invention, a biochemical assay device is provided, which includes the above-described reaction cassette and a sampling part. The sampling part includes a sampling tube configured to draw a liquid sample, an absorption compartment containing an absorption material inside thereof, and a reservoir configured to store a liquid reagent.

According to another aspect of the present invention, a biochemical assay method using the above-described biochemical assay device is provided. In one embodiment, the biochemical assay method includes the following steps: (a) storing a liquid reagent in the reservoir; (b) drawing a liquid sample using the sampling part; (c) applying a reactant material within the third space; (d) inserting the sampling part into the reaction cassette, such that the liquid sample and the liquid reagent flow into the first space and react with each other to form a first liquid mixture; (e) rotating the reaction cassette to make the first liquid mixture in the first space flows into the second space; (f) performing an optical measurement on the first liquid mixture in the second space; (g) rotating the reaction cassette to make the first liquid mixture flow into the third space and react with the reactant material to form a second liquid mixture; (h) rotating the reaction cassette to make the second liquid mixture flow into the second space; (i) performing the optical measurement on the second liquid mixture in the second space; and (j) rotating the reaction cassette to make the second liquid mixture flow into the absorption compartment of the sampling part.

The other aspects of the present invention, part of them will be described in the following description, part of them will be apparent from description, or can be known from the execution of the present invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE PICTURES

The foregoing aspects and many of the attendant advantages of this invention will become more readily appreciated as the same becomes better understood by reference to the following detailed description, when taken in conjunction with the accompanying pictures, wherein:

FIG. 5 is a perspective view illustrating the manner in which the sampling part is inserted into the reaction cassette in accordance with one embodiment of the present invention;

DETAILED DESCRIPTION OF THE INVENTION

Figure 1:
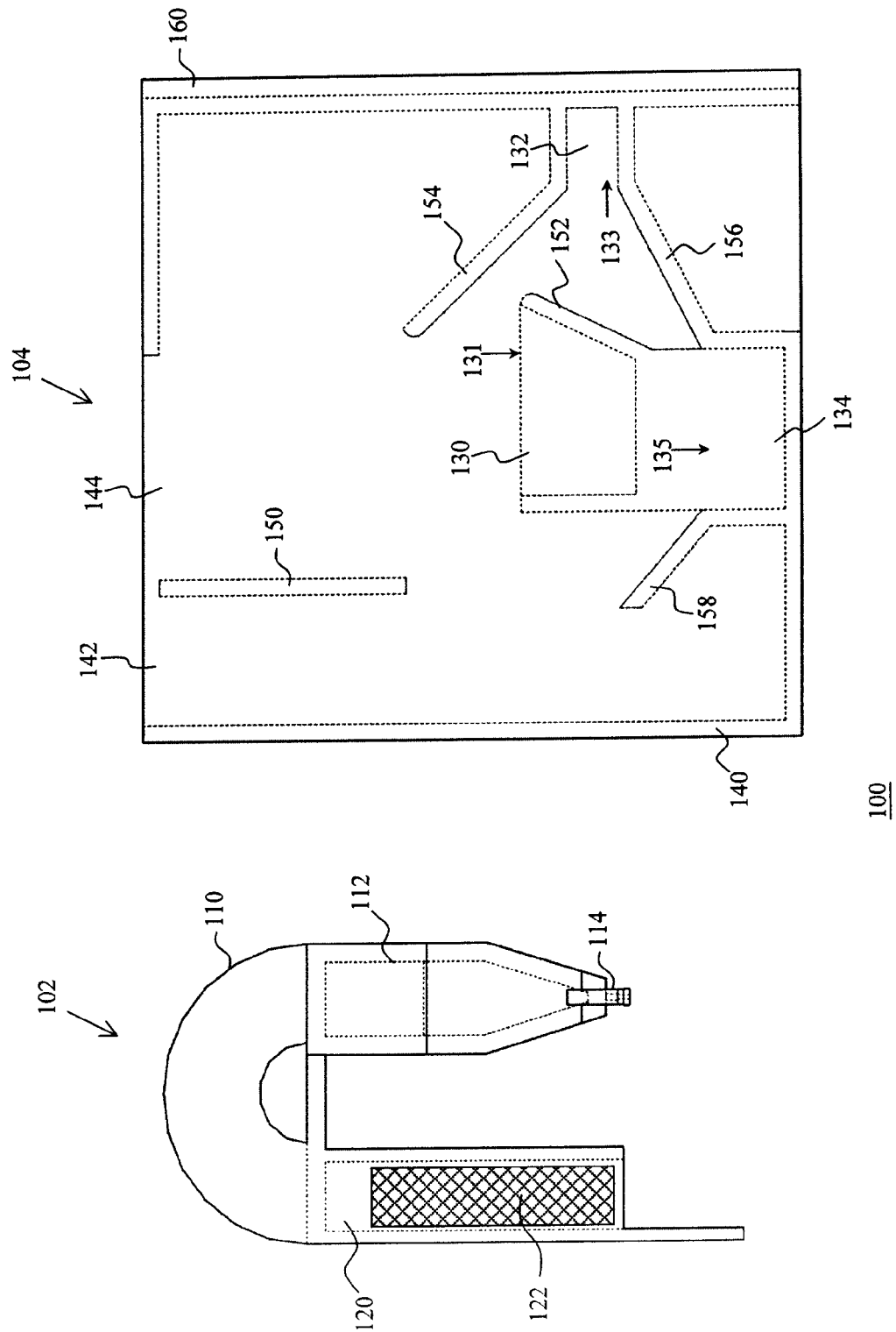
FIG. 1 illustrates a perspective view of a biochemical assay device according to an embodiment of the present invention.

The present invention discloses an assay device and an assay method using the same for carrying out the process of analyzing constituents of a liquid sample in a more convenient and safer manner. The present invention will be described more fully hereinafter with reference to the FIGS. 1-7F. However, it should be noted that the features illustrated in the drawings are not necessarily drawn to scale, and like reference numerals represent the same or similar elements. The devices, elements, and methods in the following description are configured to illustrate the present invention, and should not be construed in a limiting sense.

FIG. 1 illustrates a perspective view of a biochemical assay device 100 according to an embodiment of the present invention, which includes a sampling part 102 and a reaction cassette 104. The sampling part 102 includes a sampling tube 114, a reservoir 112 configured to store liquid reagents of various types, and an absorption compartment 120 containing an absorption material 122. The absorption compartment 120 is a hollow cylinder with an opening. The opening of the absorption compartment 120 can be arranged in the bottom of the absorption compartment 120 for facilitating extraction and insertion of the absorption material 122. The absorption material 122 can be any material of high absorptivity, such as cotton, sponge, filter paper, etc.

The sampling tube 114 is configured to draw a liquid sample (such as blood sample). Preferably, the liquid sample is drawn by capillarity into the sampling tube 114. In the embodiment that the liquid sample is a blood sample, the type of the liquid reagent stored in the reservoir 112 may vary depending on what ingredient in the blood sample is being tested (such as glucose, cholesterol, virus, etc.). For example, the liquid reagent can be antibody solution or reacting enzyme solution. The liquid reagent can be sealed inside the reservoir 112 by a piece of aluminum foil (not shown in FIG. 1; see FIG. 4B, element 416). It should be understand that the foregoing aluminum foil can be replaced by other flexible material which has deformable properties and liquid sealing function, such as plastic film and water-proof paper, etc. During the insertion of the sampling part 102 into the reaction cassette 104, the foregoing aluminum foil can be removed automatically by rubbing and scraping against the reaction cassette 104.

Further, the sampling part 102 can include a hand holder 110 for allowing a user to easily manipulate the sampling part 102. Although, as shown in FIG. 1, the hand holder 110 is preferably formed arc shape, other shapes can also be applied as long as the user can easily hold and operate the sampling part 102.

Referring to FIG. 1 again, the reaction cassette 104 includes an outer wall 140 defining an inner space and having two inlets 142 and 144 leading into the inner space. In the inner space, the reaction cassette 104 further includes an inner wall 150, an inner wall 152, and inner wall 154, an inner wall 156, an inner wall 158, a first space 130, a second space 132, and a third space 134. Each of the first space 130, the second space 132, and the third space 134 has a function of accommodating liquid.

The first space 130 has a first opening 131 and the second space 132 has a second opening 133. The first opening 131 faces upward, i.e. the direction of the first opening 131 is vertically upward, while the direction of the second opening 133 is perpendicular to the direction of the first opening 131. The first space 130 and the second space 132 are disposed such that when the reaction cassette 104 is rotated, liquid in the first space 130 can flow into the second space 132. In the embodiment shown in FIG. 1, by rotating the reaction cassette 104 clockwise, the liquid in the first space 130 can flow into the second space 132 through the inner wall 152 under the influence of gravity. The inner wall 154, being extended from the second space 132, is configured to prevent the liquid from leaking out of a desired flow path during the time that the liquid flows from the first space 130 into the second space 132. The third space 134 is located below the first space 130 and has a third opening 135 whose direction is the same as the direction of the first space 130. The inner wall 156, being connected to both of the second opening 133 and the third opening 135, functions as a liquid flow channel between the second space 132 and the third space 134.

As shown in FIG. 1, the inner wall 150 is located below both of the inlet 142 and the inlet 144 for guiding the sampling part 102 inserted into the reaction cassette 104. It should be noted that the position and the angle of the inner wall 150 may vary depending on the structure of the sampling part 102. Furthermore, the inner wall 158, being connected to the third opening 135, can function as a liquid flow channel between the third space 134 and the absorption compartment 120 when the sampling part 102 is inserted into the reaction cassette 104.

The aluminum foil enclosing the back of the sampling part 102 can be readily and easily removed when the sampling part 102 is inserted into the reaction cassette 104, such that the liquid reagent stored in the reservoir 112 and the liquid sample contained in the sampling tube 114 can flow into the first space 130. After the liquid reagent and the liquid sample are mixed and react with each other in the first space 130, the reaction cassette 104 can be rotated to allow the mixture of the liquid reagent and the liquid sample to flow from the first space 130 into the second space 132 under the force of the gravity. Subsequently, an optical measurement (such as optical density (O.D.) measurement) can be performed with respect to the mixture in the second space 132 to determine the characteristics of the mixture. Next, the reaction cassette 104 is rotated to move the mixture of the liquid reagent and the liquid sample through the inner wall 156 into the third space 134 by virtue of the gravity. The inner surface of the third space 134 is coated with a layer of reactant material (such as antibody or enzyme) in advance, such that the liquid sample, liquid reagent, and reactant material can mixed and react with each other in the third space 134. Next, the reaction cassette 104 is rotated again to move the mixture of the liquid sample, liquid reagent, and reactant material through the inner wall 156 into the second space 132, and then a second optical measurement is performed thereon. After the optical measurement is completed, the reaction cassette 104 is rotated to move the mixture through the inner walls 156 and 158 into the absorption compartment 120 of the sampling part 102 to be absorbed by the absorption material 122. Finally, the waste liquid can be easily removed from the reaction cassette 104 by drawing out the absorption material 122.

After being combined with the sampling part 102, the reaction cassette 104 can be put into a measurement instrument (not shown). The measurement instrument can rotate the reaction cassette 104 clockwise or counterclockwise according to a predetermined rule, such that the liquid sample, liquid reagent, and reactant material can mix and react with each other in sequence. Correspondingly, the reaction cassette 104 can further include an error-proof 160 for preventing the reaction cassette 104 from being placed into the measurement instrument in wrong directions. In one embodiment, the error-proof 160 is a protrusion connected to the outer wall 140.

The reaction cassette 104 can be made of glass, resin, or other transparent materials by a method well known in the art, such as injection-molding technique. In one embodiment, the reaction cassette 104 is implemented by an integral forming technique.

Figure 2:
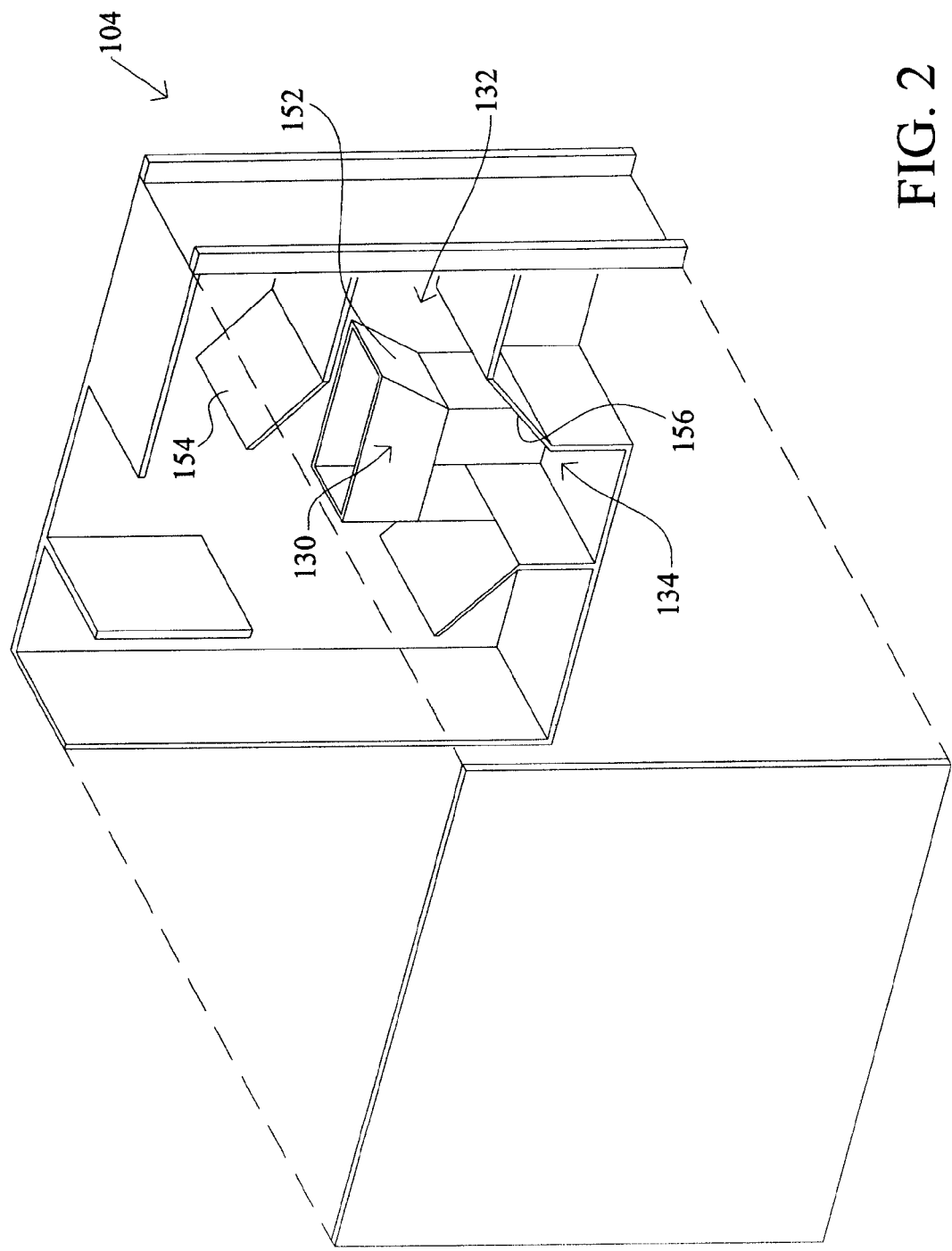
FIG. 2 shows a stereoscopic perspective view of a reaction cassette according to an embodiment of the present invention.
Figure 3:
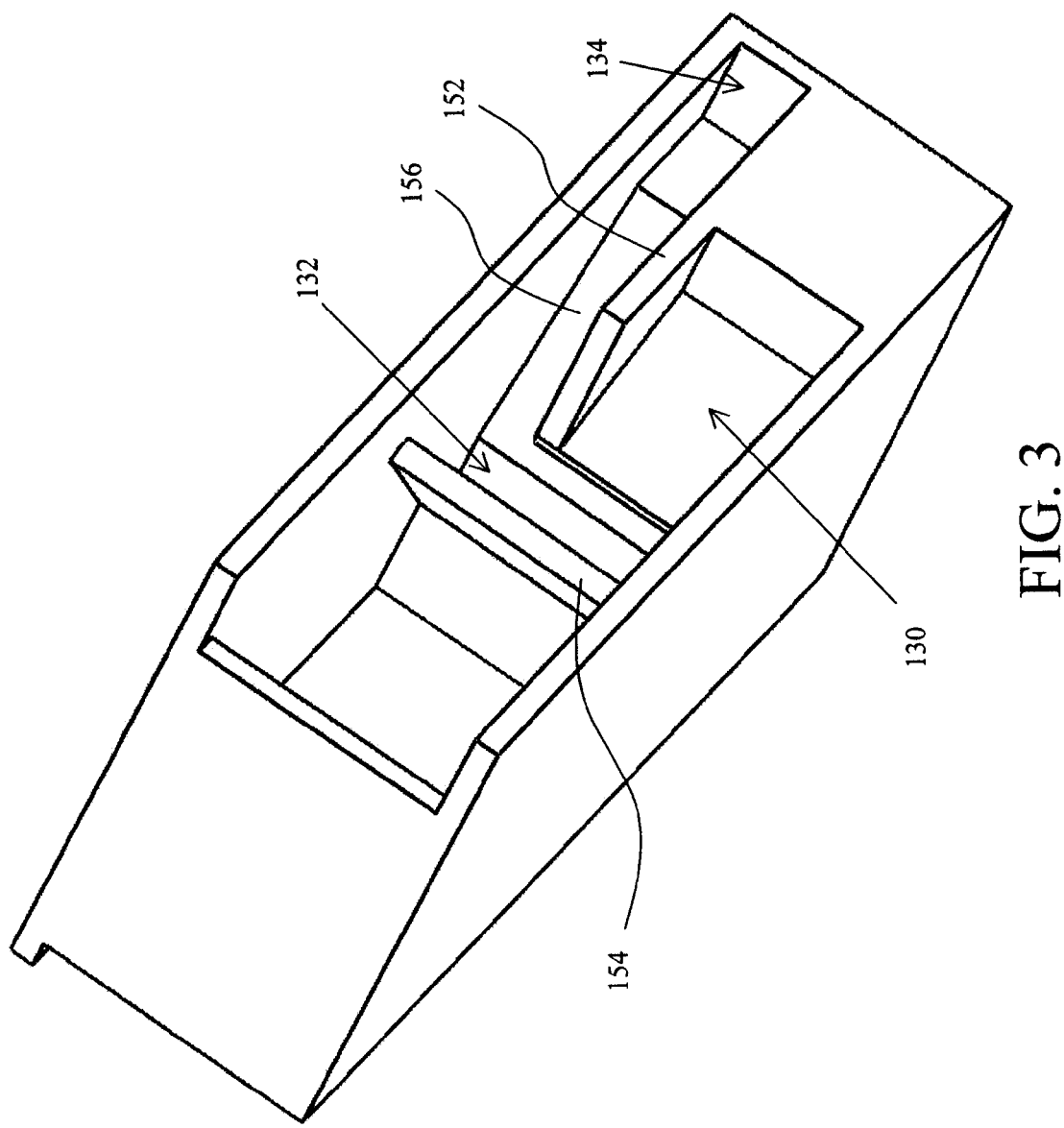
FIG. 3 shows a partial enlarged stereoscopic view of a reaction cassette according to an embodiment of the present invention.

In order to clearly illustrate the inner structure of the reaction cassette 104 shown in FIG. 1, FIGS. 2 and 3 respectively show a stereoscopic perspective view and a partial enlarged stereoscopic view of the reaction cassette 104 according to an embodiment of the present invention. As shown in FIGS. 2 and 3, multiple inner walls are arranged so as to define the first space 130, the second space 132, and the third space 134 within the reaction cassette 104. Furthermore, the inner wall 152 is one of the inner walls constituting the first space 130, the inner wall 154 is extended from the second space 132, and the inner wall 156 is connected to both of the second space 132 and third space 134.

Figure 4A:
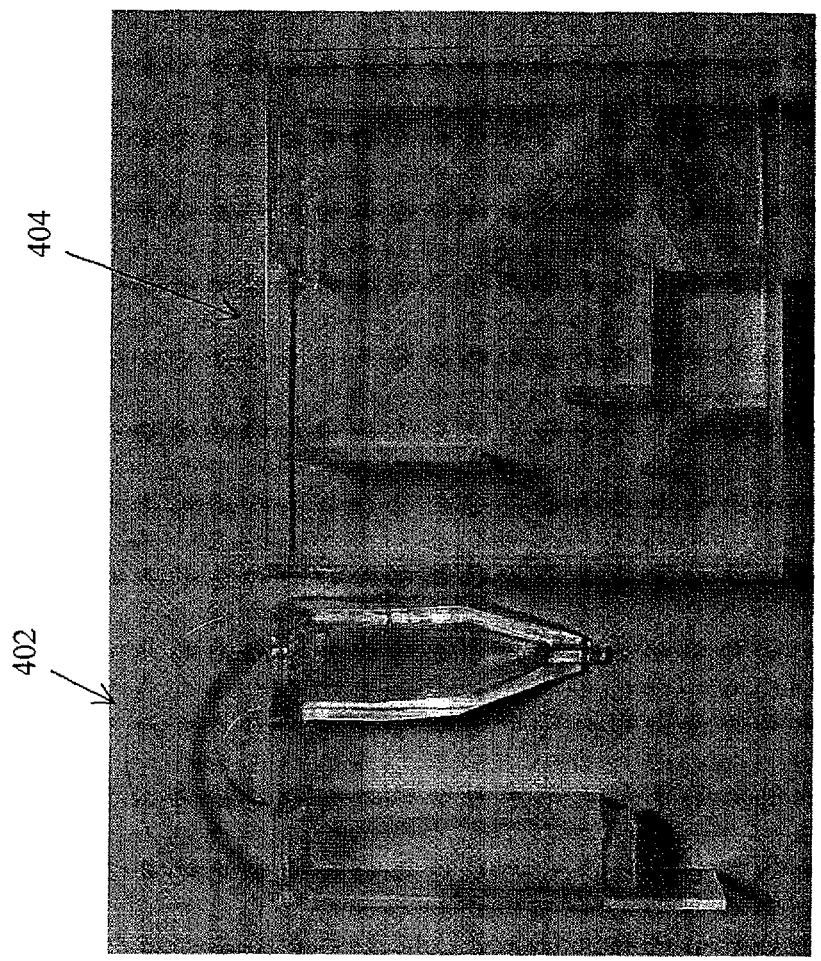
FIGS. 4A and 4B are respectively a front view photo and a back view photo of a biochemical assay device in accordance with one embodiment of the present invention.
Figure 4B:
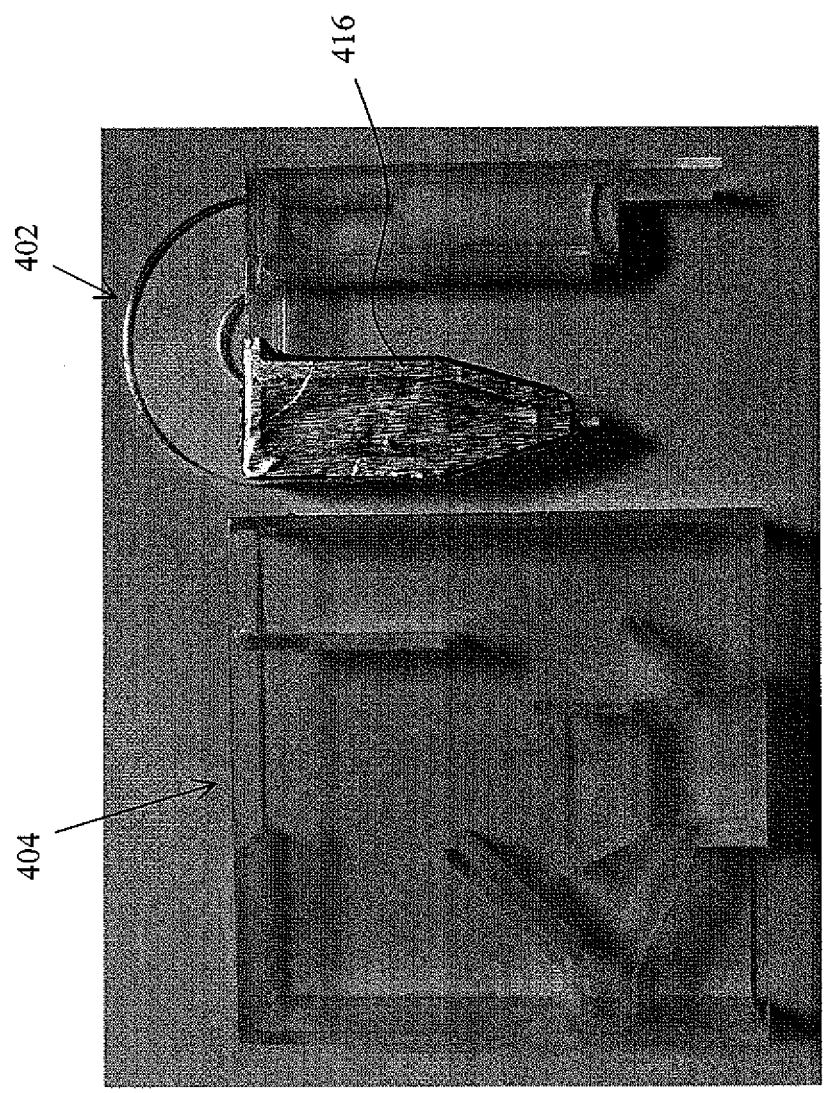

FIGS. 4A and 4B are respectively a front view photo and a back view photo of a biochemical assay device 400 in accordance with one embodiment of the present invention. In this embodiment, the biochemical assay device 400 includes a sampling part 402 and a reaction cassette 404 both made of transparent material, and the sampling part 402 further includes an aluminum foil 416 for providing a fluid-tight seal.

FIG. 5 is a perspective view illustrating the manner in which the sampling part 502 is inserted into the reaction cassette 504 in accordance with one embodiment of the present invention. Before the sampling part 502 is inserted into the reaction cassette 504, the liquid reagent and liquid sample are both contained within the sampling part 502; meanwhile, the reactant material is applied to the surface of the third space 534. When the sampling part 502 is inserted into the reaction cassette 504 in the direction indicated by arrow in FIG. 5, the seal material (such as aluminum foil) at the back of the sampling part 502 is peeled off by the outer wall of the reaction cassette 504, so as to allow the liquid reagent and the liquid sample flow downward from the sampling part 502 into the first space 530 of the reaction cassette 504.

Figure 6:
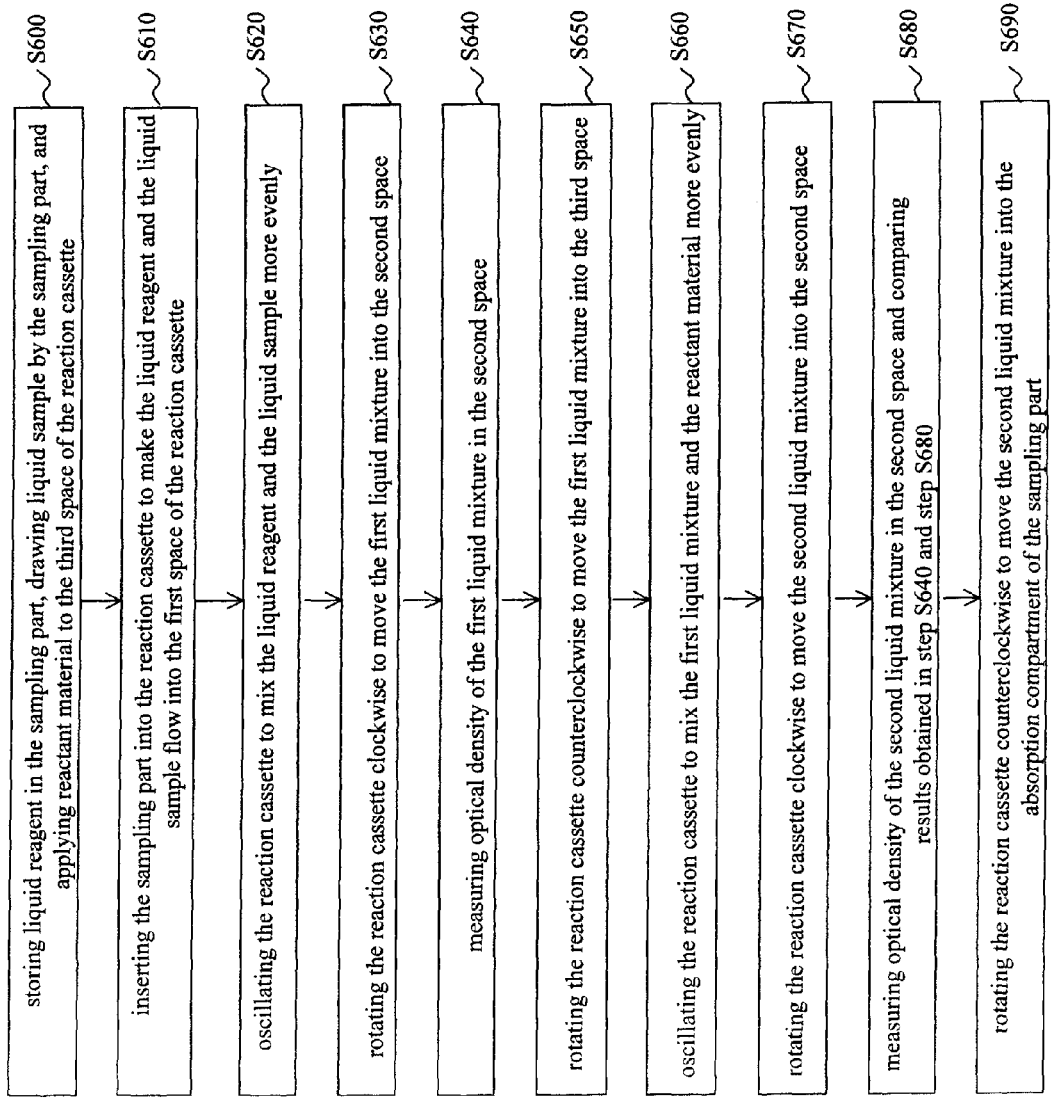
FIG. 6 is a flowchart of a biochemical assay method in accordance with one embodiment of the present invention.

FIG. 6 is a flowchart of a biochemical assay method using the biochemical assay device 100 shown in FIG. 1 in accordance with one embodiment of the present invention, and FIGS. 7A-7F are illustrative diagrams showing steps of the biochemical assay method shown in FIG. 6. Now, an embodiment of an assay method will be described in detail with reference to FIGS. 6 and 7A-7F.

Figure 7A:
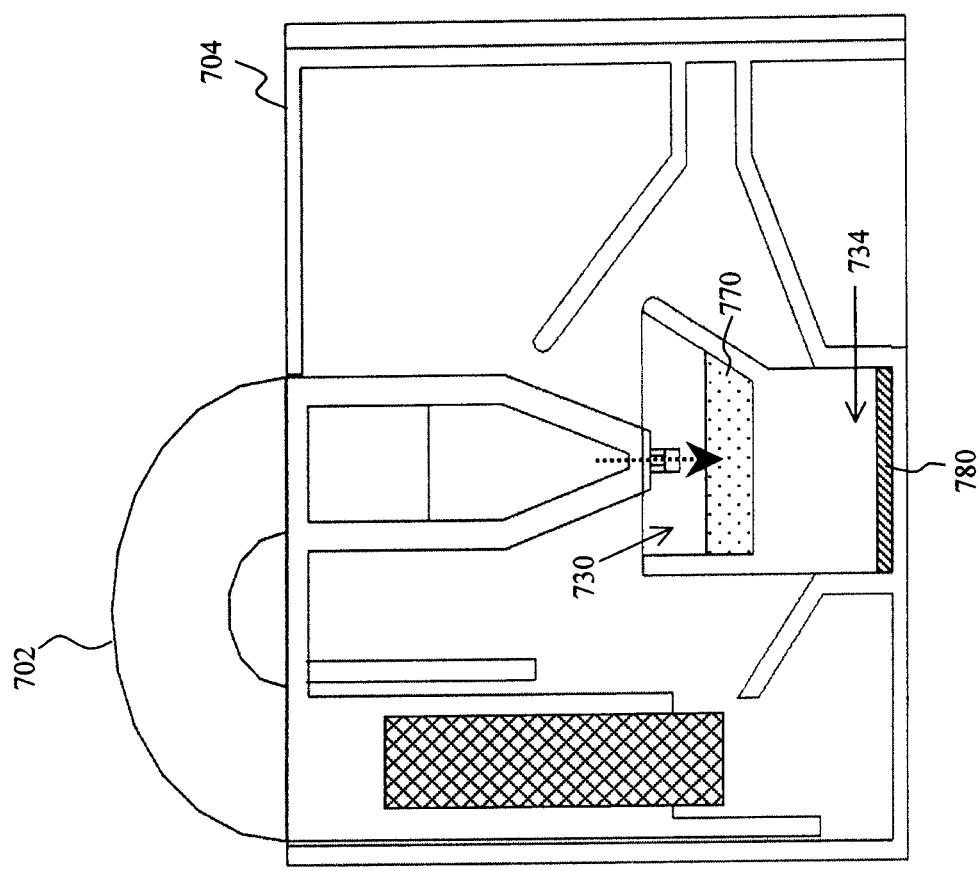
FIGS. 7A-7F are illustrative diagrams showing steps of the method shown in FIG. 6.

First, referring to FIGS. 6 and 7A, in step S600, the liquid reagent is stored in the sampling part 702, the liquid sample is drawn by the sampling part 702, and the reactant material 780 is applied to the surface of the third space 734 of the reaction cassette 704. Next, in step S610, the sampling part 702 is inserted into the reaction cassette 704, so that the liquid reagent and the liquid sample in the sampling part 702 can flow into the first space 730 of the reaction cassette 704 in the direction indicated by the arrow shown in FIG. 7A. Next, in step S620, the liquid reagent and the liquid sample can be mixed more evenly by oscillating the reaction cassette 704, which then react with each other to form a first liquid mixture 770. Typically, the reactant material 780 is a film having substantially no fluidity under ordinary conditions, and therefore does not flow during the rotation of the reaction cassette 704. In one embodiment, the reactant material 780 can be formed on the surface of the third space 734 by the known coating or spraying method.

Figure 7B:
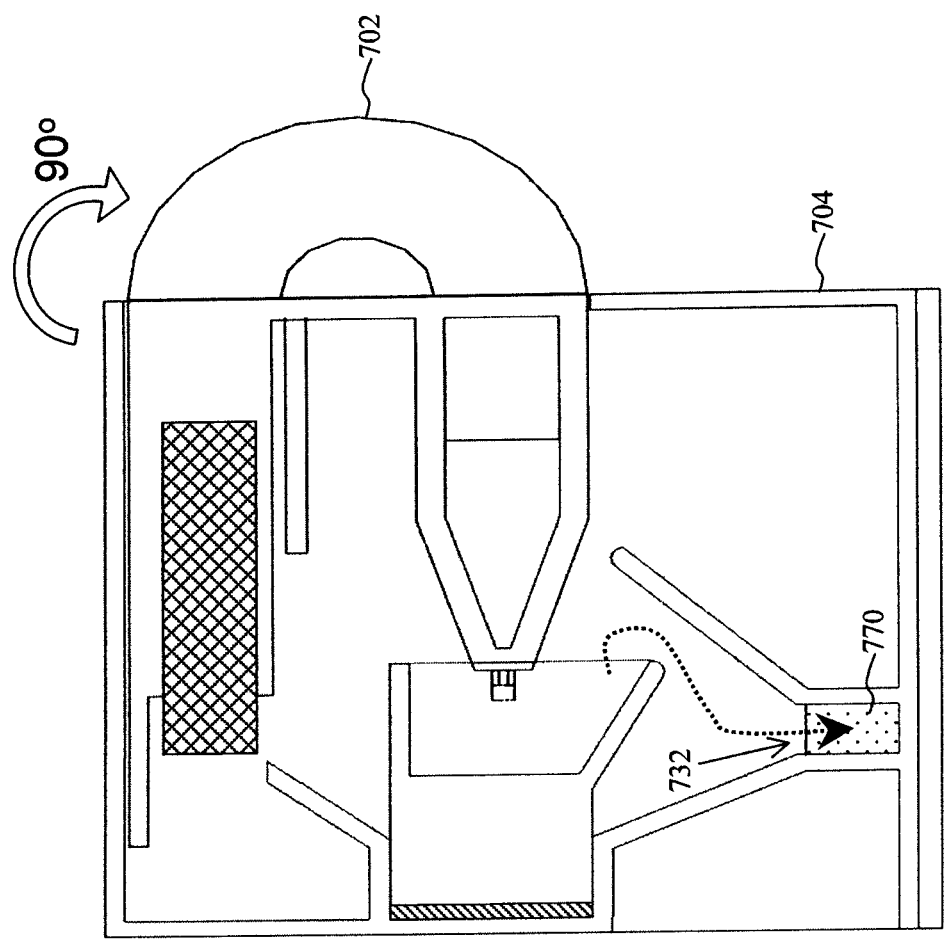
Figure 7C:
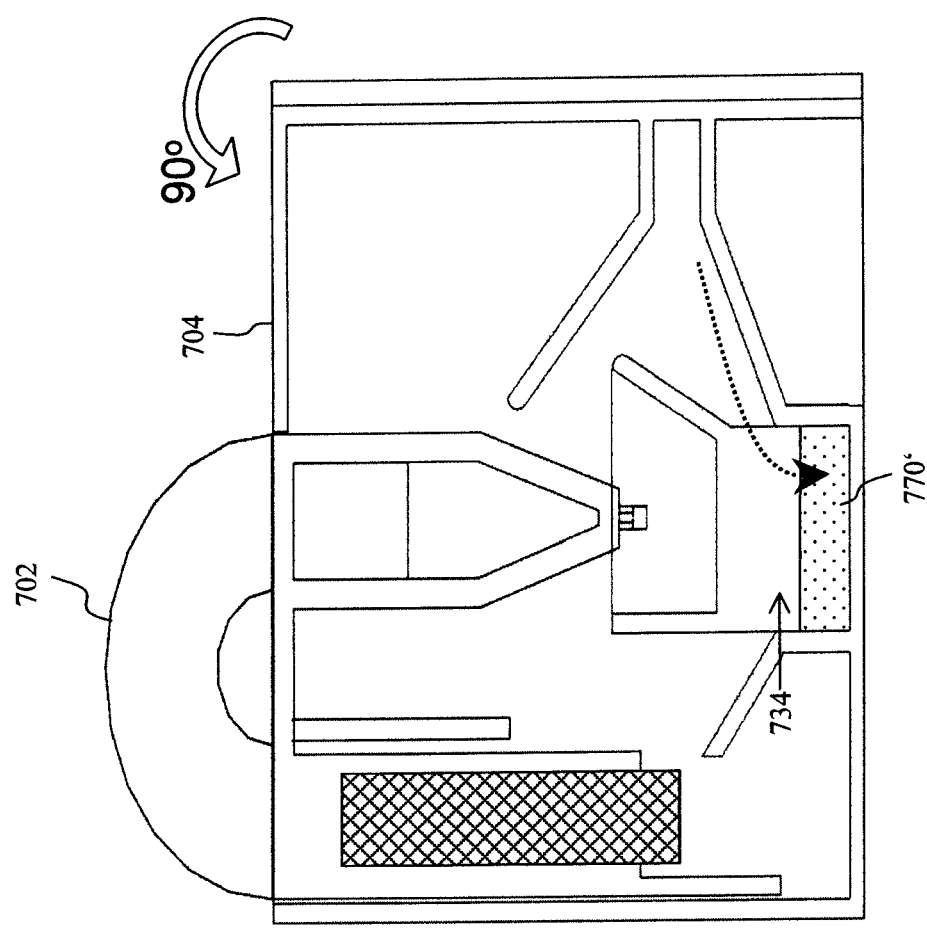
Figure 7D:
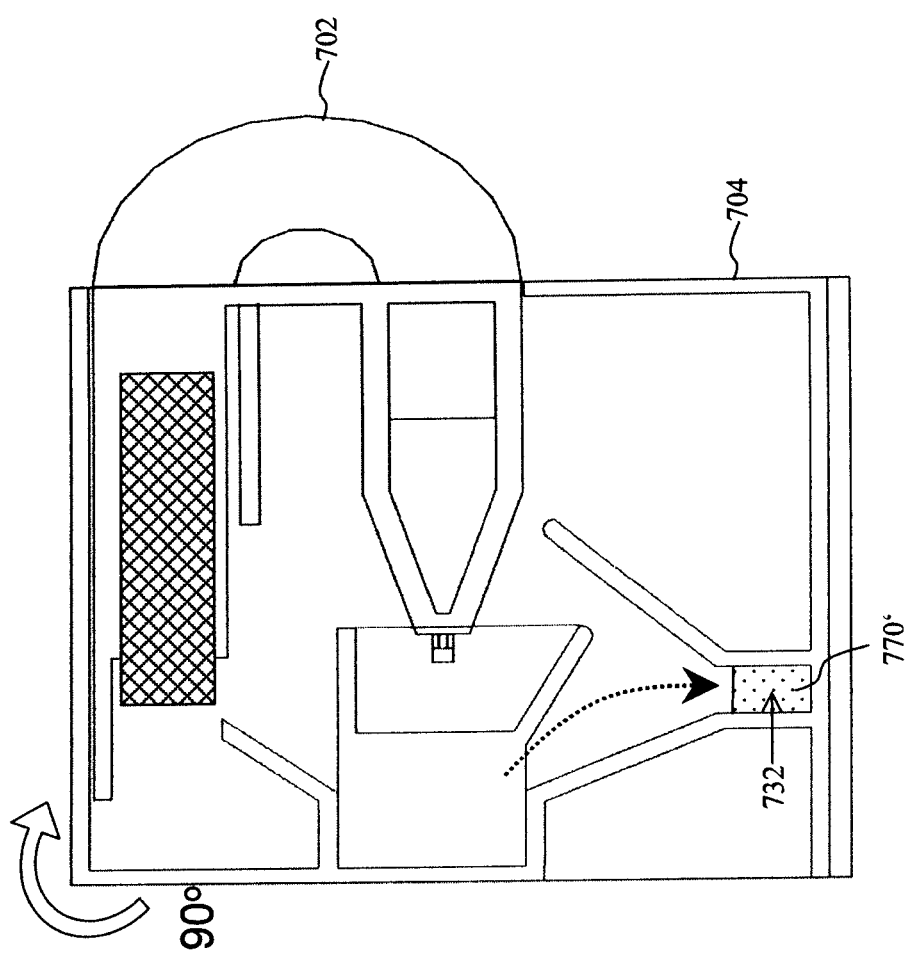

Next, referring to FIGS. 6 and 7B, in step S630, the reaction cassette 704 is rotated clockwise, whereby the first liquid mixture 770 can flow into the second space 732 of the reaction cassette 704 in the direction indicated by the arrow shown in FIG. 7B. In one embodiment, a rotation angle of the step S630 is preferably, but not limited to, about 70 degrees to about 110 degrees, and is more preferably about 90 degrees. Next, in step S640, an optical measurement is performed with respect to the first liquid mixture 770 in the second space 732. In one embodiment, the step S640 is performed to measure the optical density of the first liquid mixture 770 in the second space 732 by using a light having wavelength of 660 nm. Next, referring to FIGS. 6 and 7C, in step S650, the reaction cassette 704 is rotated counterclockwise, whereby the first liquid mixture 770 can flow into the third space 734 of the reaction cassette 704 in the direction indicated by the arrow shown in FIG. 7C. In one embodiment, a rotation angle of the step S650 is preferably, but not limited to, about 70 degrees to about 110 degrees, and is more preferably about 90 degrees.

Next, in step S660, the first liquid mixture 770 can be mixed with the reactant material 780 in the third space 734 more evenly by oscillating the reaction cassette 704, which then react with each other to form a second liquid mixture 770'. Next, referring to FIGS. 6 and 7D, in step S670, the reaction cassette 704 is rotated clockwise, whereby the second liquid mixture 770' consisted of the liquid reagent, the liquid sample, and the reactant material can flow into the second space 732 of the reaction cassette 704. In one embodiment, a rotation angle of the step S670 is preferably, but not limited to, about 70 degrees to about 110 degrees, and is more preferably about 90 degrees. Next, in step S680, an optical measurement the same as that in step S640 is performed with respect to the second liquid mixture 770' in the second space 732. In one embodiment, the step S680 is performed to measure the optical density of the second liquid mixture 770' in the second space 732 by using a light having wavelength of 660 nm. The optical signals measured in step S640 and step S680 can be converted into the electrical signals for subsequent analysis and comparison, so as to determine a ratio or a concentration of a specific ingredient in the liquid sample. Since both the optical measurements in step S640 and step S680 are performed in the second space 732, the measurement deviation caused by variations in the transparency or transmittance of the material of the reaction cassette 704 can be cancelled out.

Figure 7E:
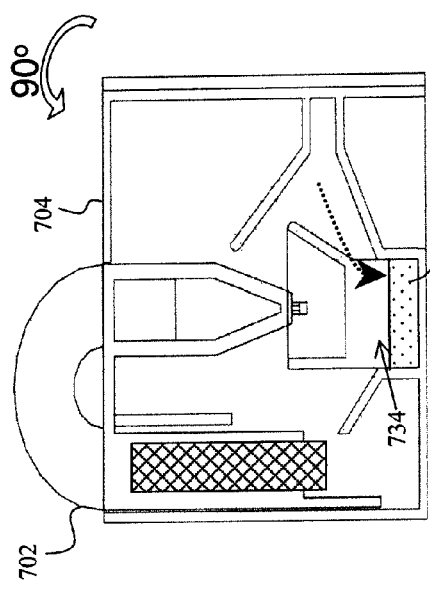
Figure 7F:
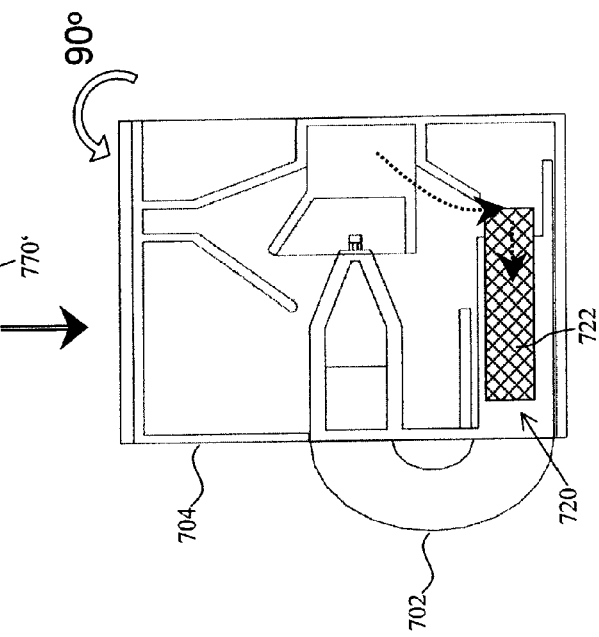

Next, referring to FIGS. 6, 7E and 7F, in step S690, the reaction cassette 704 is rotated counterclockwise, whereby the second liquid mixture 770' can flow into the third space 734 and then into the absorption compartment 720 of the sampling part 702. Therefore, the second liquid mixture 770' can be absorbed by the absorption material 722 of the absorption compartment 720, so as to prevent environmental pollution and harm to human bodies caused by escaping waste liquid. In one embodiment, a rotation angle of the step S690 is preferably, but not limited to, about 160 degrees to about 200 degrees, and is more preferably about 180 degrees.

During the measurement process, the rotation of reaction cassette 704 can be performed automatically by a measurement instrument (not shown) according to a predetermined rule, such that the liquid sample, liquid reagent, and reactant material can be moved from one space to another space in the reaction cassette 704 in a desired sequence for carrying out the reaction and measurement steps. Therefore, user's operation load can be reduced through the method shown in FIGS. 6 and 7A-7F, for example, the user's manipulation of adding reagents to the liquid sample is not needed. On the other hand, since the rotation angle in each step can be about 90 degrees and about 180 degrees, which allows easy operation, the rotation steps of the assay method can be done manually and readily even when the measurement instrument is not available. Further, the waste liquid remaining after the assay procedure can be easily collected and handled by rotating the reaction cassette 704. To sum up, the assay device and the assay method disclosed in the present specification can increase user convenience, reduce man-made errors, and provide an easy and secure way for treatment of waste liquid.

The above illustration is for preferred embodiments of the present invention, is not limited to the claims of the present invention. Equivalent amendments and modifications without departing from the spirit of the invention should be included in the scope of the following claims.

The invention claimed is:

1. A reaction cassette for biochemical assay, comprising:
a first space configured to accommodate liquid and having a first opening, a direction of the first opening being directed upward;
a second space having a second opening, a direction of the second opening being perpendicular to the direction of the first opening;
a third space located below the first space and having a third opening, a direction of the third opening being the same as the direction of the first space; and
an inner wall, connected with the second opening and the third opening, acting as a liquid flow channel between the second space and the third space.

2. The reaction cassette according to claim 1, wherein the reaction cassette is made of transparent material.

3. The reaction cassette according to claim 1, further comprising an outer wall defining an inner space, wherein the first space, the second space, the third space, and the inner wall are disposed within the inner space, and the outer wall comprising an inlet located above the first space.

4. The reaction cassette according to claim 3, further comprising a protrusion connecting with the outer wall for preventing the reaction cassette from being placed into a measurement instrument in wrong directions.

5. A biochemical assay device, comprising:
a reaction cassette for biochemical assay, comprising:
a first space configured to accommodate liquid and having a first opening, a direction of the first opening being directed upward;
a second space having a second opening, a direction of the second opening being perpendicular to the direction of the first opening;
a third space located below the first space and having a third opening, a direction of the third opening being the same as the direction of the first space; and
an inner wall, connected with the second opening and the third opening, acting as a liquid flow channel between the second space and the third space; and
a sampling part removably insertable into the reaction cassette, comprising:
a sampling tube configured to draw a liquid sample;
an absorption compartment containing an absorption material inside thereof; and
a reservoir configured to store a liquid reagent.

6. The biochemical assay device according to claim 5, wherein the sampling part is inserted into the reaction cassette through the inlet, and the reaction cassette further comprises:
a second inner wall, connected with the third space, acting as a liquid flow channel between the third space and the absorption compartment; and
a third inner wall located below the inlet for guiding the sampling part into the reaction cassette.

7. The biochemical assay device according to claim 5, wherein the reservoir of the sampling part is sealed by an aluminum foil, and the aluminum foil is removed during insertion of the sampling part into the reaction cassette.

8. The biochemical assay device according to claim 5, wherein the reservoir of the sampling tube of the sampling part is in fluid communication with the reaction cassette with the sampling part removably inserted into the reaction cassette.

9. The reaction cassette according to claim 1, wherein the first opening and the second opening are positioned to allow a liquid contained in the first space to flow into the second space.

10. The biochemical assay device according to claim 5, wherein the first opening and the second opening are positioned to allow a liquid contained in the first space to flow into the second space.

11. A biochemical assay method, comprising:
(a) providing a biochemical assay device, comprising:
a reaction cassette of claim for biochemical assay, comprising:
a first space configured to accommodate liquid and having a first opening, a direction of the first opening being directed upward;
a second space having a second opening, a direction of the second opening being perpendicular to the direction of the first opening;
a third space located below the first space and having a third opening, a direction of the third opening being the same as the direction of the first space; and
an inner wall, connected with the second opening and the third opening, acting as
a liquid flow channel between the second space and the third space; and
a sampling part removably insertable into the reaction cassette, comprising:
a sampling tube configured to draw a liquid sample;
an absorption compartment containing an absorption material inside thereof; and
a reservoir configured to store a liquid reagent;
(b) storing the liquid reagent in the reservoir;
(c) drawing the liquid sample using the sampling tube;
(d) inserting the sampling part into the reaction cassette, such that the liquid sample and the liquid reagent flow into the first space and react with each other to form a first liquid mixture;
(e) rotating the reaction cassette to make the first liquid mixture in the first space flow into the second space;
(f) performing an optical measurement on the first liquid mixture in the second space;
(g) rotating the reaction cassette to make the first liquid mixture flow into the third space and react with a reactant material in the third space to form a second liquid mixture;
(h) rotating the reaction cassette to make the second liquid mixture flow into the second space; and
(i) performing the optical measurement on the second liquid mixture in the second space.

12. The biochemical assay method according to claim 11, further comprising:
- (j) rotating the reaction cassette to make the second liquid mixture flow into the absorption compartment of the sampling part.

13. The biochemical assay method according to claim 12, wherein the step (e) is to rotate the reaction cassette clockwise to make the first liquid mixture flow into the second space, the step (g) is to rotate the reaction cassette counterclockwise to make the first liquid mixture flow into the third space, the step (h) is to rotate the reaction cassette clockwise to make the second liquid mixture flow into the second space, and the step (j) is to rotate the reaction cassette counterclockwise to make the second liquid mixture flow into the absorption compartment of the sampling part.

14. The biochemical assay method according to claim 13, wherein the step (e) is to rotate about 70 degrees to about 110 degrees clockwise, the step (g) is to rotate about 70 degrees to about 110 degrees counterclockwise, the step (h) is to rotate about 70 degrees to about 110 degrees clockwise, and the step (j) is to rotate about 160 degrees to about 200 degrees counterclockwise.

15. The biochemical assay method according to claim 11, further comprising a step before the step (d):
- applying the reactant material to the third space.

* * * * *